(12) United States Patent
Gubernick et al.

(10) Patent No.: US 7,589,249 B2
(45) Date of Patent: Sep. 15, 2009

(54) MULTIPLE ZONE APERTURED WEB

(75) Inventors: David Gubernick, Cherry Hill, NJ (US); William G. F. Kelly, Middlesex, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 186 days.

(21) Appl. No.: 10/217,794

(22) Filed: Aug. 13, 2002

(65) Prior Publication Data

US 2003/0125687 A1 Jul. 3, 2003

Related U.S. Application Data

(63) Continuation-in-part of application No. 10/317,381, filed on Dec. 12, 2002, which is a continuation of application No. 09/783,844, filed on Feb. 15, 2001, now abandoned.

(51) Int. Cl.
*A61F 13/15* (2006.01)

(52) U.S. Cl. ................ 604/378; 604/385.101; 604/383

(58) Field of Classification Search ............. 604/378, 604/385.101, 383, 380; 428/131, 140, 170–172
See application file for complete search history.

(56) References Cited

U.S. PATENT DOCUMENTS

| | | | |
|---|---|---|---|
| 2,958,366 A | 11/1960 | Conti | |
| 3,054,148 A | 9/1962 | Zimmerli | |
| 4,041,948 A | 8/1977 | Flam et al. | |
| 4,056,103 A | 11/1977 | Kaczmarzyk et al. | |
| 4,100,324 A | 7/1978 | Anderson et al. | |
| 4,305,391 A | 12/1981 | Jackson | |
| 4,323,069 A * | 4/1982 | Ahr et al. ............ | 604/378 |
| 4,609,518 A | 9/1986 | Baird | |
| 4,695,422 A | 9/1987 | Curro et al. | |
| 4,710,186 A | 12/1987 | DeRossett et al. | |
| 4,741,877 A | 5/1988 | Mullane, Jr. | |
| 4,816,100 A | 3/1989 | Friese | |
| 4,859,273 A | 8/1989 | Friese | |
| 4,863,450 A | 9/1989 | Friese | |
| 5,264,268 A | 11/1993 | Luceri et al. | |
| 5,342,334 A | 8/1994 | Thompson et al. | |
| 5,403,300 A | 4/1995 | Howarth | |
| 5,458,835 A | 10/1995 | Wilkes et al. | |
| 5,567,376 A | 10/1996 | Turi et al. | |
| 5,591,149 A * | 1/1997 | Cree et al. ............ | 604/378 |
| 5,634,914 A | 6/1997 | Wilkes et al. | |
| 5,647,862 A | 7/1997 | Schmitz | |
| 5,916,462 A | 6/1999 | James et al. | |
| 6,183,436 B1 | 2/2001 | Korteweg et al. | |
| 6,465,713 B1 | 10/2002 | Gell et al. | |
| 6,570,055 B2 | 5/2003 | Yang et al. | |
| 2001/0014348 A1 | 8/2001 | Schoelling | |

FOREIGN PATENT DOCUMENTS

DE 1 560 128 A 2/1971

(Continued)

OTHER PUBLICATIONS

PCT International Search Report PCT/US02/25672 dated Dec. 13, 2002.

*Primary Examiner*—Jacqueline F. Stephens

(57) ABSTRACT

The invention provides an apertured web comprising multiple, discrete zones comprising arrangements of land areas and at least two apertures.

20 Claims, 8 Drawing Sheets

FOREIGN PATENT DOCUMENTS

| | | |
|---|---|---|
| EP | 0 165 807 A | 12/1985 |
| EP | 0 295 957 A | 12/1988 |
| EP | 0 301 874 A | 2/1989 |
| EP | 0 456 281 A | 11/1991 |
| EP | 0 685 215 A | 12/1995 |
| EP | 0 738 505 A | 10/1996 |
| EP | 0 761 190 A | 3/1997 |
| EP | 0 841 156 A | 5/1998 |
| EP | 0 960 611 A | 12/1999 |
| FR | 2 725 360 A | 4/1996 |
| GB | 495461 A | 11/1938 |
| GB | 855537 A | 12/1960 |
| GB | 2 310 606 A | 9/1997 |
| JP | 11155902 A | 6/1999 |
| WO | WO 97/23185 A | 7/1997 |
| WO | WO97/40793 A | 11/1997 |
| WO | WO 98/20825 A | 5/1998 |
| WO | WO 98/46182 A | 10/1998 |
| WO | WO 99/00096 A | 1/1999 |
| WO | WO 99/26769 A | 6/1999 |
| WO | WO 99/32061 A | 7/1999 |
| WO | WO 99/53879 A | 10/1999 |
| WO | WO 01/01909 A | 1/2001 |

* cited by examiner

MULTIPLE ZONE APERTURED WEB

CROSS-REFERENCE TO RELATED APPLICATIONS

This application claims the benefit of U.S. provisional application 60/312,330 filed on Aug. 14, 2001, and is a continuation-in-part of U.S. application Ser. No. 09/783,844, filed on Feb. 15, 2001, now abandoned, which claims foreign priority under 35 USC 119 to DE 100 06 961.4-45 filed on Feb. 16, 2000.

FIELD OF THE INVENTION

The present invention relates to apertured webs suitable for use as topsheets or other fluid transporting layers in absorbent articles such as sanitary napkins and tampons. In particular, an apertured web topsheet receiving the liquids to be absorbed comprises at least two different, discrete, and visually distinct zones. These zones allow for the use of a single topsheet with different fluid passage characteristics and different tactile and visual characteristics within different zones of the topsheet.

BACKGROUND OF THE INVENTION

Sanitary articles such as sanitary napkins, baby diapers, absorbent inserts, tampons, and absorbent adult incontinence articles are well-known in the art. Typically all these articles comprise a wearer facing surface and a garment facing surface. The wearer facing surface receives from the wearer of such articles bodily discharges such as urine, vaginal discharges or menses, to be absorbed. In order for the article to store the liquid, the wearer facing surface has to be liquid permeable while maintaining the integrity of the outer wearer facing surface of the absorbent article and preventing liquid absorbed by the article from flowing back out onto a wearer. This wearer facing surface is provided by a topsheet.

Well-known topsheets in the art of absorbent articles are non-woven fabrics and films. Non-woven fabrics are made of fibers which by their nature provide non-linear apertures for liquid transport, although such fabrics may further be modified with an arrangement of apertures. Films have to be rendered permeable by aperturing.

Films suitable for use as topsheets are generally made of polymeric material and typically comprise apertures or orifices which have been engineered to provide certain characteristics. These apertures are defined by sidewalls, which extend from the surface of the film. The apertures may vary in shape and size but have commonly been provided in a single preferred size and shape. An example of such a known topsheet is described in U.S. Pat. No. 3,929,135 to Thompson, incorporated herein by reference. The sidewalls of the apertures define the amount of extension, if any, beyond the plane of the film thickness and the direction of such extensions. The sidewalls of the apertures also can be provided in the shape of a funnel.

Film topsheets are preferred over fabric topsheets by some users since they can provide a relatively cleaner-looking surface even after liquid has passed through since they do not generally retain liquids on their surfaces. However, some users may find film topsheets to be irritating or chafing, especially along the edges of the product, since the pattern (i.e., the size, shape, and spacing) of apertures provided by the topsheet extends across the entire topsheet, and the aperture pattern that is preferred for passing fluid quickly may not be preferred for facing against the user's inner thighs along the side edges of the product.

A method that has been used to overcome the disadvantages of side edge discomfort while retaining the benefits of quick fluid passage is that of using an apertured film topsheet over the entire surface of the absorbent product, and then covering the apertured film along the side edges of the product with a layer of nonwoven fabric. The apertured film provides good fluid handling properties in the center of the product where the fluid enters, and the nonwoven imparts greater comfort to the user by providing soft fabric along the product's edges. However, this adds material cost to the product and an extra step in the manufacturing process.

An additional disadvantage of known apertured films is that, because of their uniform aperture patterns, their fluid transport properties are generally uniform as well. Attempts have been made to improve the fluid transport characteristics of certain apertured films by the inclusion of larger apertures in and amongst the apertures of the uniform aperture pattern. However, this method still produces an apertured film with a uniform aperture arrangement, albeit an arrangement consisting of large holes and small holes. Furthermore, although the larger apertures may allow for the passage of fluid into an underlying absorbent layer, these same larger apertures may be more likely to allow the absorbed fluid to pass back out of the apertures when the wetted absorbent layer is subjected to pressure. In other words, absorbed fluid may be squeezed out of the absorbent layer, through the large holes, and onto the skin of a wearer of the absorbent article.

It is therefore an object of this invention to provide an apertured web suitable for use as an absorbent article topsheet with two or more different and discrete, that is, noncontinuous and individually distinct, zones within a single topsheet.

DESCRIPTION OF THE INVENTION

Figure 1:
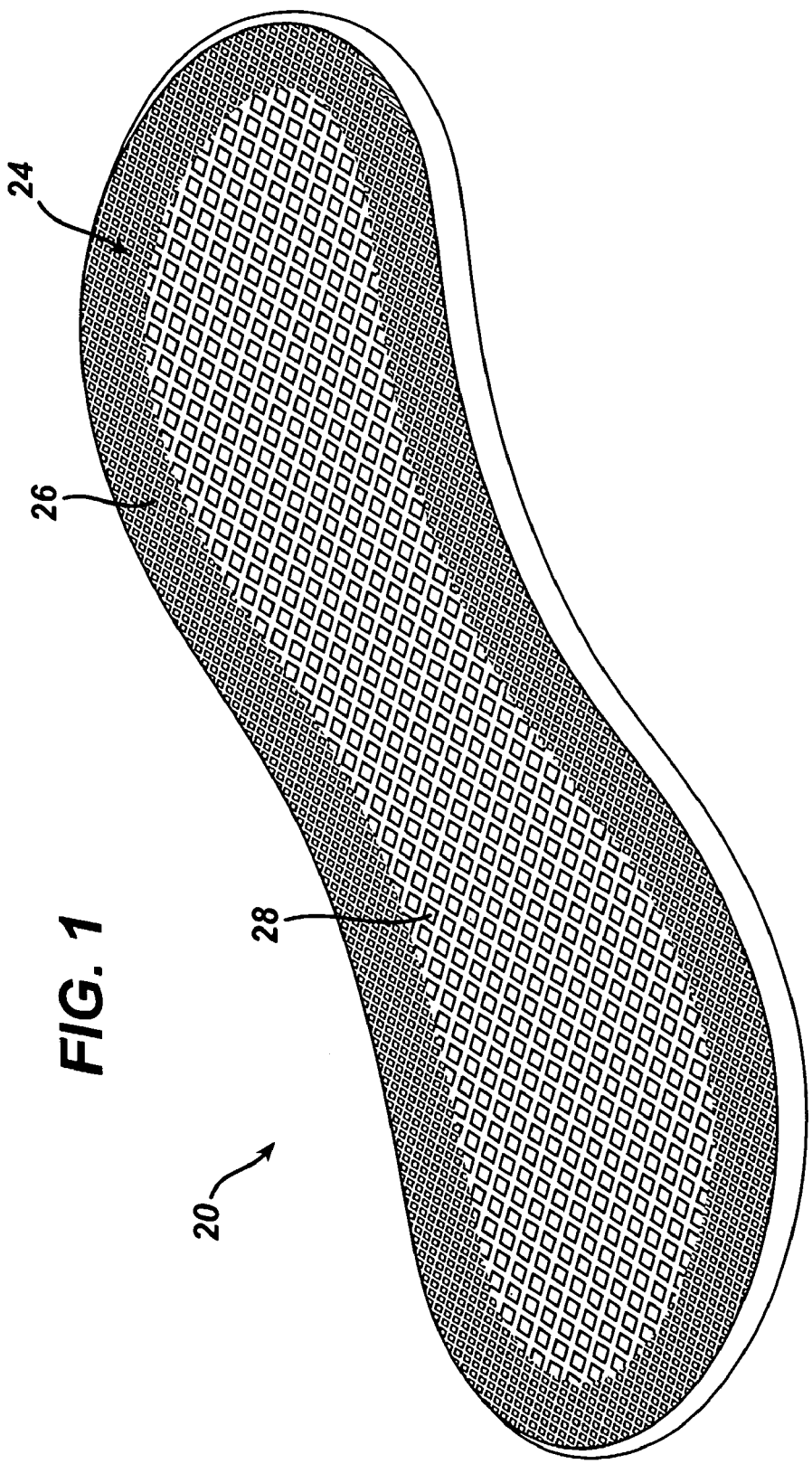
FIG. 1 is a top plan view of a sanitary napkin having a topsheet comprising an embodiment of the apertured web of the present invention.

Referring now to the drawings, an absorbent article 20 having a topsheet 24 comprising an example of an apertured web of the present invention is shown in plan view in FIG. 1.

It can be seen from FIG. 1 that the apertured web of topsheet 24 has first zone 26 and second zone 28. First zone 26 is separate and distinct from second zone 28, that is, the first zone does not overlap the second zone. First zone 26 has a first arrangement of land areas and at least two apertures, and second zone 28 has a second arrangement of land areas and at least two apertures. The arrangement of land areas and at least two apertures of one zone does not continue into the other zone; i.e., the zones are discrete and separate.

The two zones are differentiated by their respective arrangements of apertures and land areas and the boundary between the first zone and the second zone may be defined as the place where the first arrangement ends and the second arrangement begins. Since the two arrangements are different, the boundary between them is not a natural border; that is, one arrangement does not naturally flow into the other arrangement. The boundary may be created by abruptly ending one arrangement and beginning another arrangement, or in some cases, by "morphing" the edges of the arrangements where they meet to form a boundary. Morphing means that the edges of the adjoining arrangements are modified slightly to allow for the arrangements to adjoin without abruptly ending one arrangement and beginning another arrangement, such as might occur if a cut edge of one arrangement were simply joined to a cut edge of another arrangement. Such morphed edges ease the transition from one arrangement to an adjoining arrangement. Morphed edges also help to prevent roughness in the boundary or weakness in the web in the boundary area. However, even when the edges are morphed, the boundary between the arrangements remains visually distinct. As used herein, "visually distinct" means visibly different to a normal, unaided, human eye at a distance of 12 inches between the eye and a visible object.

In the example shown in FIG. 1, the first arrangement 26 ends and the second arrangement 28 begins along a boundary between the two arrangements. However, in alternate embodiments of the invention, the boundary between the two arrangements may have a third arrangement which is distinct and different from either the first or the second arrangements, or the boundary may be free of an arrangement of land areas and apertures.

Each zone is defined by an arrangement of land areas and at least two apertures, which provide the zone with an overall visual appearance. As used herein, "arrangement" means the specific size, distance, and orientation relationships among the land area and the at least two apertures in each zone. The arrangement may consist of one size or more than one size of aperture. Such an arrangement provides a zone with a distinct unified visual appearance, with no distinct break in its visual appearance, i.e., no separate arrangement. Thus each arrangement be regular, irregular, random, repeating, nonrepeating, geometric, or nongeometric. As used herein, "regular" means recurring at fixed or regular intervals. "Irregular" as used herein, means not recurring at fixed or regular intervals. By "geometric" is meant an arrangement based on rectilinear or curvilinear motifs or outlines.

The apertured web of the present invention has at least two zones, each having an arrangement of land areas and at least two apertures. The zones are separated by a visibly distinct boundary.

Figure 2:
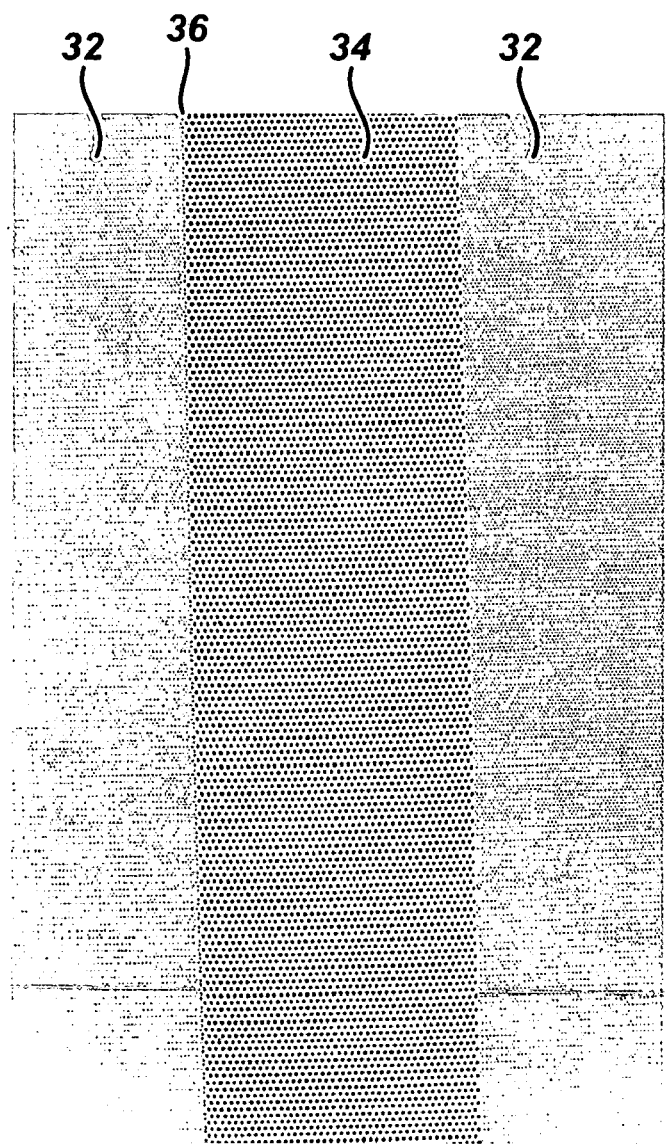
FIG. 2 is an embodiment of an apertured web of the present invention.

Referring now to FIG. 2, an embodiment of an apertured web of the invention is shown. The first zone 32 has a first arrangement with a regular array of very small apertures, and the second zone 34 has a second arrangement with a regular array of somewhat larger apertures. When this apertured web is used as a topsheet on, for example, a sanitary napkin, the second zone 34 is positioned so that the incoming fluid tends to enter the article through the second zone. Thus, an arrangement of somewhat larger apertures is preferred for the second zone in this embodiment. In such a construction, the first zone 32 would be positioned along the side edges of the sanitary napkin, where smoothness against the inner thighs and groin area are a concern. The smaller aperture hole size and finer arrangement would provide a smoother surface in the first zone of this embodiment.

Figure 3:
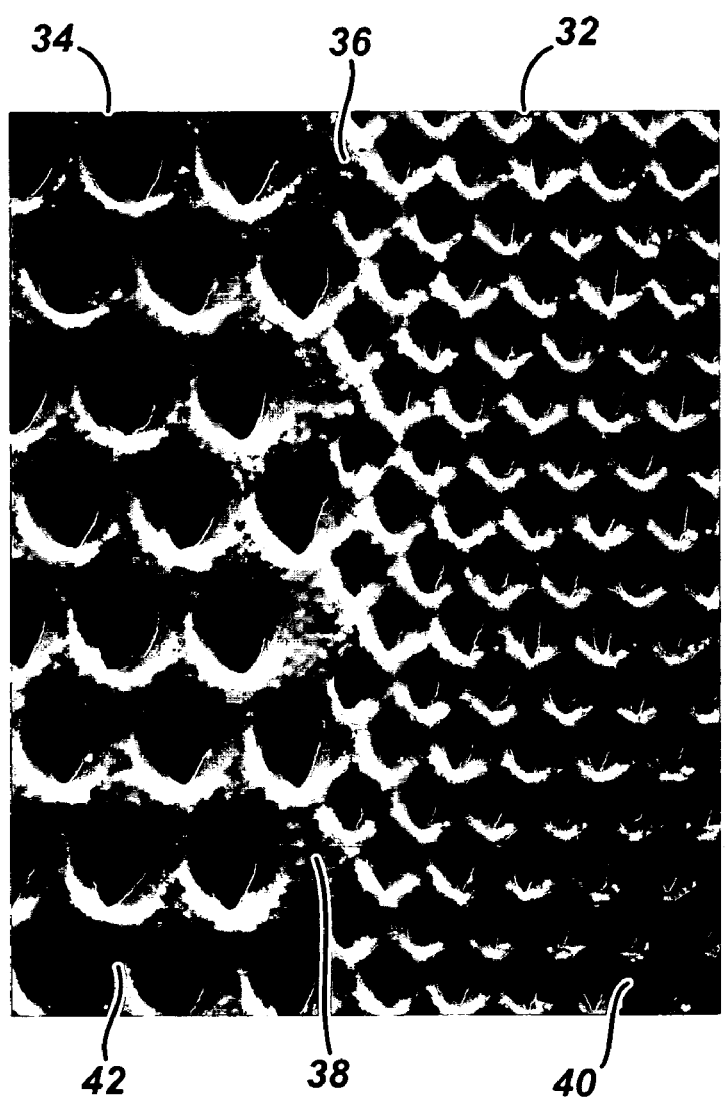
FIG. 3 is a photomicrograph of a portion of the apertured web shown in FIG. 2.

FIG. 3 shows a photomicrograph of a portion of the apertured web shown in FIG. 2. In particular, the portion of the web shown in FIG. 3 shows a portion of first zone 32, a portion of second zone 34, and a portion of the boundary 36 that separates first zone 32 from second zone 34. It can be seen in FIG. 3, that the boundary 36 is created by morphing the arrangement of the first zone 32 and the second zone 34. That is, the land areas 38 of the boundary are a different size and shape than the land areas 40 of the first zone 32 or the land areas 42 of the second zone 34.

Alternatively, another embodiment of an apertured web suitable for use as a topsheet on a sanitary napkin may have an arrangement of relatively smaller apertures in a central fluid-contacting region and relatively larger apertures along the sides of the napkin. In such a case, the aperture size in the central region may be chosen to allow the passage of fluid, and the aperture size along the sides may be chosen to minimize the land area of the arrangement and thus minimize contact with the skin of a wearer of such a napkin.

Figure 4:
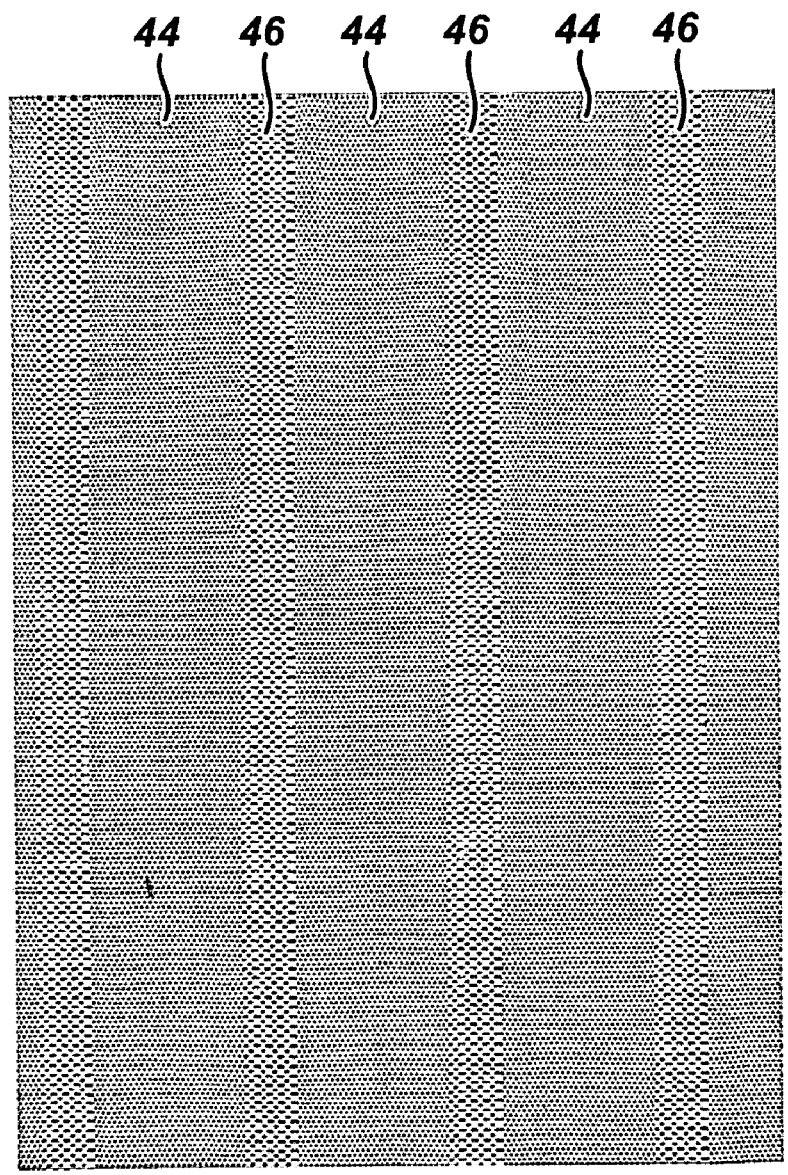
FIG. 4 is another embodiment of an apertured web of the present invention.

FIG. 4 shows another embodiment of an apertured web of this invention. The web shown in FIG. 4 has first zone 44 and second zone 46 in alternating arrangement. Such a web may be suitable for use as a topsheet on an absorbent article, such as a diaper or a sanitary napkin, where the alternating zones tend to distribute incoming fluid over the topsheet for passage through the topsheet and into an underlying absorbent material. Such distribution helps to utilize more of the absorbent material than if incoming fluid passed directly through the apertured web at its point of impact. Utilization of more of the absorbent material helps to prevent leakage of fluid out of the product and to prevent puddling, or wetness of the topsheet caused by oversaturation of the underlying absorbent material and passage of previously absorbed fluid back through to the surface of the topsheet.

The apertured web shown in FIG. 4 is also suitable for use as a topsheet on a catamenial tampon. The web may be slit so that second zone 46 overlies the center of the tampon's outer surface, and first zone 44 overlies the outer surface of the leading end and the trailing end of the tampon.

Figure 5:
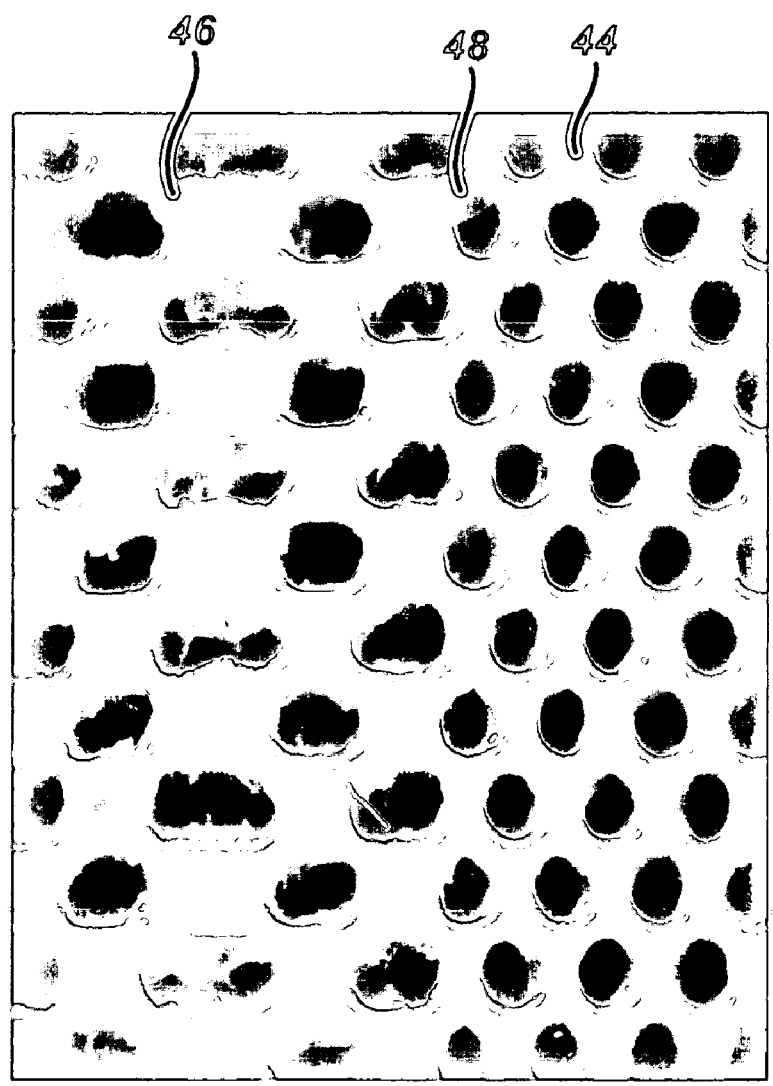
FIG. 5 is a photomicrograph of a portion of the apertured web shown in FIG. 4.

FIG. 5 is a photomicrograph of a portion of the apertured web of FIG. 4. First zone 44 and second zone 46 are separated from one another by boundary 48. It can be seen that first zone 44 and second zone 46 are discrete and separate from one another with neither arrangement of land areas and apertures continuing into the other arrangement.

Figure 6:
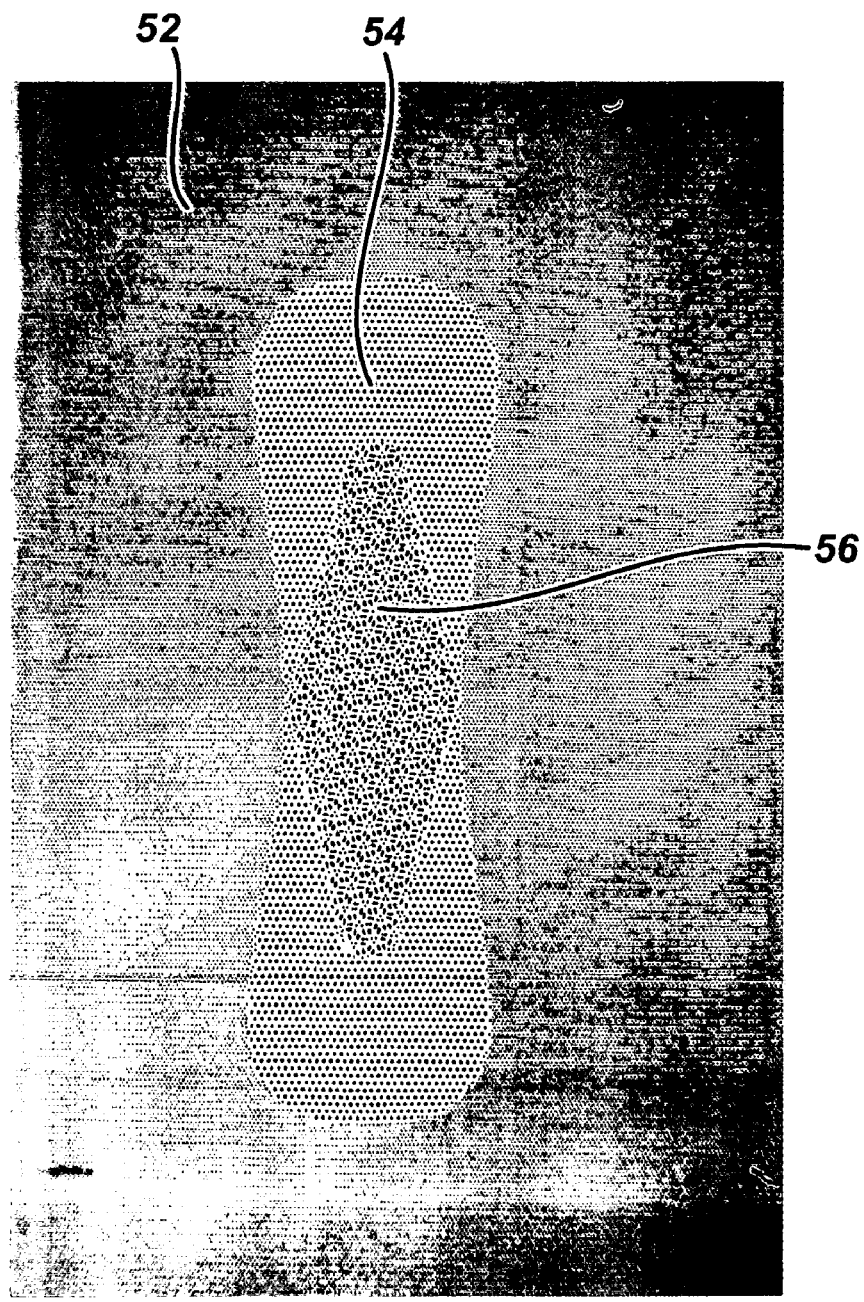
FIG. 6 is yet another embodiment of an apertured web of the present invention.

Referring now to FIG. 6, an embodiment of an apertured web is shown with first zone 52, second zone 54, and third zone 56. The embodiment shown in FIG. 6 is suitable for use as a topsheet or other fluid passage layer in an absorbent article such as a sanitary napkin or a diaper. In such a use, third zone 56 is positioned in the region of the article where fluid tends to enter the article, and thus, the arrangement of land areas and apertures of third zone 56 is chosen to pass fluid quickly and provide a dry surface to a wearer of the article. The arrangement of second zone 54 is chosen to provide a comfortable surface to a wearer and to pass any fluid that is not passed by third zone 56. The arrangement of first zone 56 comprises small apertures, which present a smooth silky surface to the skin of a wearer.

Figure 7:
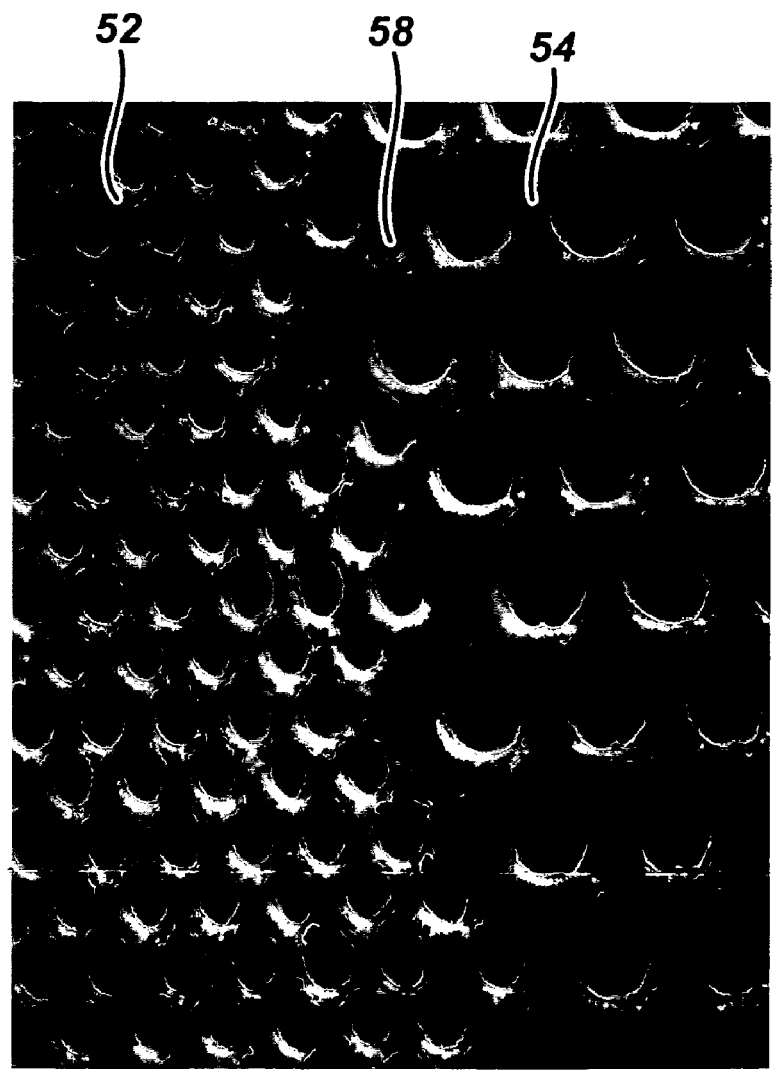
FIG. 7 is a photomicrograph of a portion of the apertured web shown in FIG. 6.

FIG. 7 is a photomicrograph of a portion of the apertured web of FIG. 6, showing first zone 52 and second zone 54 separated from one another by boundary 58.

Figure 8:
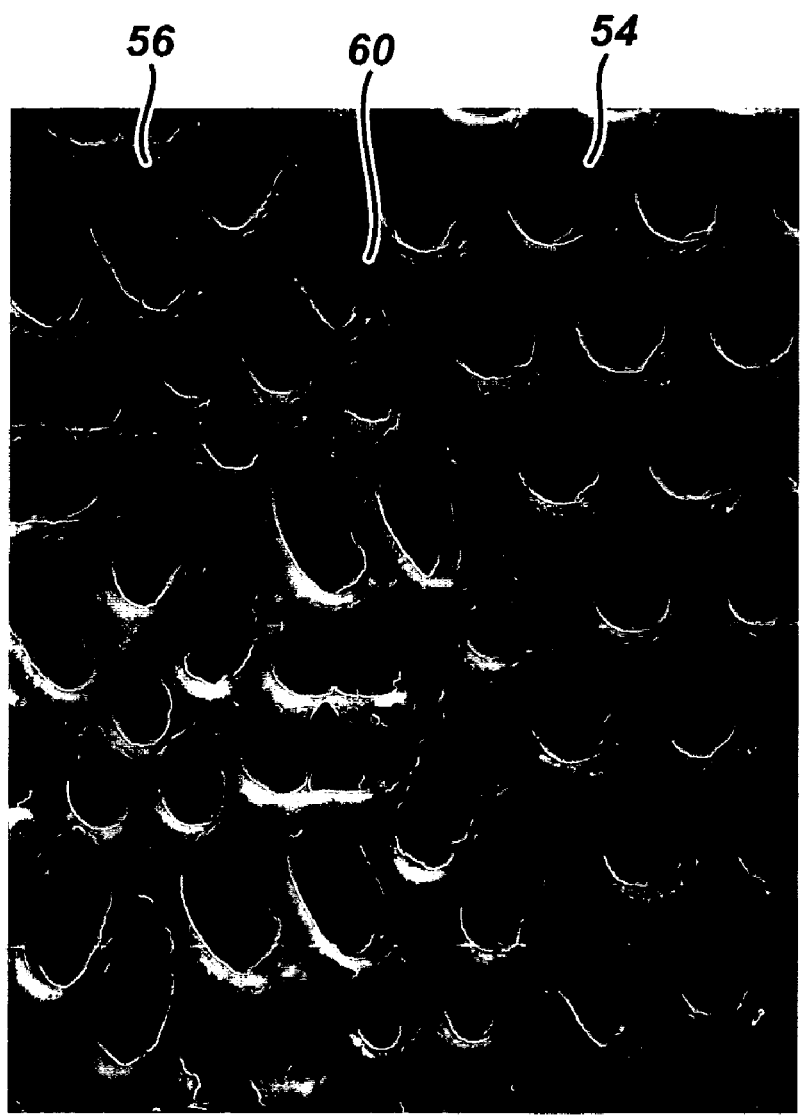
FIG. 8 is a photomicrograph of another portion of the apertured web shown in FIG. 6.

FIG. 8 is a photomicrograph of another portion of the apertured web of FIG. 6, showing second zone 54 and third zone 56 separated from one another by boundary 60.

In another embodiment, a first zone may have an arrangement of land areas and at least two apertures so spaced that said arrangement is larger in dimension than the space defined by the boundary separating the first zone from a second zone. In other words, the arrangement is not repeated within the zone.

The apertured webs of the present invention may comprise nonwovens or films. A suitable film is a thin, continuous, uninterrupted film of thermoplastic polymeric material. This film may be vapor permeable or vapor impermeable; it may be embossed or unembossed; it may be corona-discharge treated on one or both of its major surfaces or it may be free of such corona-discharge treatment; it may be treated with a surface active agent after the film is formed or before the film is formed by incorporating the surface active agent as a blend into the thermoplastic polymeric material. The film may comprise any thermoplastic polymeric material including, but not limited to, polyolefins, such as high density polyethylene, linear low density polyethylene, low density polyethylene, polypropylene; copolymers of olefins and vinyl monomers, such as copolymers of ethylene and vinyl acetate or vinyl chloride; polyamides; polyesters; polyvinyl alcohol and copolymers of olefins and acrylate monomers such as copolymers of ethylene and ethyl acrylate and ethylenemethacrylate. Films comprising mixtures of two or more of such polymeric materials may also be used. The machine direction (MD) and cross direction (CD) elongation of the starting film to be apertured should be at least 100% as determined according to ASTM Test No. D-882 as performed on an Instron test apparatus with a jaw speed of 50 inches/minute (127 cm/minute). The thickness of the starting film is preferably uniform and may range from about 0.5 to about 5 mils or about 0.0005 inch (0.0013 cm) to about 0.005 inch (0.076 cm). Coextruded films can be used, as can films that have been modified, e.g., by treatment with a surface active agent. The starting film can be made by any known technique, such as casting, extrusion, or blowing.

Suitable nonwovens may include nonwoven fabrics made from any of a variety of known fibers. The fibers may vary in length from a quarter of an inch or less to an inch and a half or more. It is preferred that when using the shorter fibers (including wood pulp fiber) that the short fibers be blended with longer fibers. The fibers may be any of the well known artificial, natural or synthetic fibers, such as cotton, rayon, nylon, polyester, polyolefin, or the like. The web may be formed by any of the various techniques well known in the art, such as carding, air laying, wet laying, melt-blowing, spunbonding and the like.

A method of aperturing the web of the invention involves placing the web onto the surface of a patterned support member. The web is subjected to a high fluid pressure differential as it is on the support member. The pressure differential of the fluid, which may be liquid or gaseous, causes the web to assume the surface pattern of the patterned support member. If the patterned support member has apertures therein, portions of the web overlying the apertures may be ruptured by the fluid pressure differential to create an apertured web. A method of forming an apertured fibrous web is described in detail in commonly owned U.S. Pat. No. 5,827,597 to James et al., incorporated herein by reference.

An apertured film of this invention may be formed by placing a thermoplastic film across the surface of an apertured support member with an arrangement of apertures. A stream of hot air is directed against the film to raise its temperature to cause it to be softened. A vacuum is then applied to the film to cause it to conform to the shape of the surface of the support member. Portions of the film lying over the apertures in the support member are ruptured to create apertures in the film.

An apertured support member suitable for making the multiple zone apertured webs of this invention is made by raster scan drilling, as described in U.S. Pat. No. 5,916,462 to James et al., which is incorporated herein by reference.

While several embodiments and variations of the present invention are described in detail herein, it should be apparent that the disclosure and teachings of the present invention will suggest many alternative designs to those skilled in the art.

What is claimed is:

1. An apertured web comprising a first zone having a first arrangement of land areas and at least two apertures having the same size and shape as each other, and a second zone having a second arrangement of land areas and at least two apertures having the same size and shape as each other, but different in size or shape than the apertures of the first zone, wherein the first arrangement does not continue into the second zone and the second arrangement does not continue into the first zone.

2. The web of claim 1 wherein the web comprises a film.

3. The web of claim 1 wherein the first arrangement is regular.

4. The web of claim 1 wherein the first arrangement is irregular.

5. The web of claim 1 wherein the first arrangement is repeating.

6. The web of claim 1 wherein the first arrangement is nonrepeating.

7. The web of claim 1 wherein the first arrangement is geometric.

8. The web of claim 1 wherein the web comprises fibers.

9. The web of claim 8 wherein the web comprises staple fibers.

10. The web of claim 8 wherein the web comprises a nonwoven fabric.

11. The web of claim 1 wherein the web is a composite of a film and a nonwoven fabric.

12. The web of claim 1 wherein the first arrangement is morphed along a boundary between the first zone and the second zone.

13. The web of claim 1 further comprising at least one third zone comprising a third arrangement of land areas and at least two apertures.

14. An absorbent article comprising an apertured web comprising a first zone having a first arrangement of land areas and at least two apertures having the same size and shape as each other, and a second zone having a second arrangement of land areas and at least two apertures having the same size and shape as each other, but different in size or shape than the apertures of the first zone, wherein the first arrangement does not continue into the second zone and the second arrangement does not continue into the first zone.

15. The absorbent article of claim 14 wherein the absorbent article is a sanitary napkin.

16. The absorbent article of claim 14 wherein the absorbent article is a diaper.

17. The absorbent article of claim 14 wherein the absorbent article is a tampon.

18. The absorbent article of claim 14 wherein the apertured web comprises a body-facing topsheet.

19. The absorbent article of claim 14, wherein said apertured web further comprises at least one third zone comprising a third arrangement of land areas and at least two apertures.

20. An apertured web comprising a first zone comprising a first arrangement of land areas and at least two apertures, and a second zone comprising a second arrangement of land areas and at least two apertures, wherein the first arrangement does not continue into the second zone the second arrangement does not continue into the first zone, and said first arrangement is morphed along a boundary between the first zone and the second zone.

* * * * *

UNITED STATES PATENT AND TRADEMARK OFFICE
CERTIFICATE OF CORRECTION

PATENT NO. : 7,586,249 B2  Page 1 of 1
APPLICATION NO. : 10/217794
DATED : September 15, 2009
INVENTOR(S) : David Gubernick and William G. F. Kelly It is certified that error appears in the above-identified patent and that said Letters Patent is hereby corrected as shown below:

Title Page; should read

Related U.S. Application Data

(63) Continuation-in-part of application No. 09/783,844, filed on February 15, 2001, now abandoned.

(60) Provisional application 60/312,330 filed on August 14, 2001.

and insert;

-- Foreign Priority 35 USC 119

(30) DE 100 06 961.4-45 filed on February 16, 2000 --

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,589,249 B2                                        Page 1 of 1
APPLICATION NO. : 10/217794
DATED : September 15, 2009
INVENTOR(S) : David Gubernick et al.

It is certified that error appears in the above-identified patent and that said Letters Patent is hereby corrected as shown below:

This certificate supersedes the Certificate of Correction issued on September 21, 2010 that contained a typographical error in the patent number. The patent number was incorrectly listed as 7,586,249 in the heading of the issued cofc. The corrections in the September 21, 2010 Certificate of Correction that belonged to Patent No. 7,589,249 are as follows:

Title Page; should read

Related U.S. Application Data

(63) Continuation-in-part of application No. 09/783,844, filed on February 15, 2001, now abandoned.

(60) Provisional application 60/312,330 filed on August 14, 2001.

and insert;

-- Foreign Priority 35 USC 119

(30) DE 100 06 961.4-45 filed on February 16, 2000 --

Signed and Sealed this

Second Day of November, 2010

David J. Kappos
*Director of the United States Patent and Trademark Office*